(12) United States Patent
Malvolti et al.

(10) Patent No.: US 6,967,017 B1
(45) Date of Patent: Nov. 22, 2005

(54) FORMULATIONS OF STEROID SOLUTIONS FOR INHALATORY ADMINISTRATION

(75) Inventors: Chiara Malvolti, Parma (IT); Raffaella Garzia, Parma (IT); Gaetano Brambilla, Parma (IT); Paolo Chiesi, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 393 days.

(21) Appl. No.: 10/030,101

(22) PCT Filed: Jul. 20, 2000

(86) PCT No.: PCT/EP00/06916

§ 371 (c)(1),
(2), (4) Date: May 3, 2002

(87) PCT Pub. No.: WO01/07014

PCT Pub. Date: Feb. 1, 2001

(30) Foreign Application Priority Data

Jul. 23, 1999 (IT) .............................. MI99A1625

(51) Int. Cl.[7] .......................... A61K 9/12; A61K 9/72; A61L 9/04
(52) U.S. Cl. .................. 424/45; 424/434; 424/489; 424/450; 424/198.1
(58) Field of Search ........................... 424/45, 46, 434, 424/489, 450, 198.1

(56) References Cited

U.S. PATENT DOCUMENTS

| | | |
|---|---|---|
| 3,361,306 A | 1/1968 | Grim |
| 3,622,053 A | 11/1971 | Ryden |
| 4,185,100 A | 1/1980 | Rovee et al. |
| 4,499,108 A | 2/1985 | Sequeira et al. |
| 4,835,145 A | 5/1989 | MacDonald |
| 5,192,528 A | 3/1993 | Radhakrishnan et al. |
| 5,415,853 A | 5/1995 | Hettche et al. |
| 5,435,297 A | 7/1995 | Klein |
| 5,605,674 A | 2/1997 | Purewal et al. |
| 5,642,728 A | 7/1997 | Andersson et al. |
| 5,653,961 A | 8/1997 | McNally et al. |
| 5,676,930 A | 10/1997 | Jager |
| 5,683,677 A | 11/1997 | Purewal et al. |
| 5,695,743 A | 12/1997 | Purewal et al. |
| 5,891,419 A | 4/1999 | Cutie |
| 5,954,047 A | 9/1999 | Armer et al. |
| 5,955,058 A | 9/1999 | Jager et al. |
| 6,004,537 A * | 12/1999 | Blondino et al. ............. 424/45 |
| 6,006,745 A | 12/1999 | Marecki et al. |
| 6,026,808 A | 2/2000 | Armer et al. |
| 6,045,778 A | 4/2000 | Jager et al. |
| 6,045,784 A | 4/2000 | Ruebusch et al. |
| 6,131,566 A | 10/2000 | Ashurst |
| 6,143,277 A | 11/2000 | Ashurst et al. |
| 6,149,892 A | 11/2000 | Britto |
| 6,150,418 A | 11/2000 | Hochrainer et al. |
| 6,241,969 B1 * | 6/2001 | Saidi et al. ................... 424/45 |
| 6,253,762 B1 | 7/2001 | Britto |
| 6,290,930 B1 | 9/2001 | Blondino et al. |
| 6,315,985 B1 | 11/2001 | Wu et al. |
| 6,413,496 B1 | 7/2002 | Goodman et al. |
| 6,451,285 B2 | 9/2002 | Blondino et al. |
| 6,645,466 B1 | 11/2003 | Keller et al. |
| 6,713,047 B1 | 3/2004 | Lewis et al. |
| 6,716,414 B2 | 4/2004 | Lewis et al. |
| 2001/0031244 A1 | 10/2001 | Lewis et al. |
| 2003/0066525 A1 | 4/2003 | Lewis et al. |
| 2003/0077230 A1 | 4/2003 | Blondino et al. |
| 2003/0089369 A1 | 5/2003 | Lewis et al. |
| 2003/0157028 A1 | 8/2003 | Lewis et al. |
| 2003/0190287 A1 | 10/2003 | Lewis et al. |
| 2003/0190289 A1 | 10/2003 | Lewis et al. |
| 2003/0206870 A1 | 11/2003 | Lewis et al. |
| 2004/0047809 A1 | 3/2004 | Lewis et al. |
| 2004/0062720 A1 | 4/2004 | Lewis et al. |
| 2004/0096399 A1 | 5/2004 | Lewis et al. |
| 2004/0184993 A1 | 9/2004 | Lewis et al. |

FOREIGN PATENT DOCUMENTS

| | | |
|---|---|---|
| EP | 0 372 777 | 6/1990 |
| EP | 0 504 112 A2 | 9/1992 |
| EP | 0 642 992 A2 | 3/1995 |
| EP | 0 653 204 | 5/1995 |
| EP | 0 911 048 | 4/1999 |
| GB | 1 525 181 | 9/1978 |
| GB | 2 326 334 | 12/1998 |
| WO | WO 91/11173 | 8/1991 |
| WO | WO 92/11236 | 7/1992 |
| WO | WO 92/20391 | 11/1992 |
| WO | WO 93/05765 | 4/1993 |
| WO | WO 93/11743 | 6/1993 |

(Continued)

OTHER PUBLICATIONS

Davis, S.S. Physico-chemical studies on aerosol solutions for drug delivery I. water-propylene glycol systems. International Journal of Pharmaceutics, 1 (1978) 71-83.*

(Continued)

Primary Examiner—Gary Kunz
Assistant Examiner—Mina Haghighatian
(74) Attorney, Agent, or Firm—Oblon, Spivak, McClelland, Maier & Neustadt, P.C.

(57) ABSTRACT

The present invention relates to optimized formulations of antiinflammatory steroids for nebulisation and a process for the preparation thereof. More particularly, the invention relates to formulations for monodose or multidose vials in the form of preservative-free stable solutions of a more acceptable osmolarity, which can effectively be nebulised with the nebulisers currently available on the market and are well-tolerated by patients.

14 Claims, No Drawings

FOREIGN PATENT DOCUMENTS

| | | |
|---|---|---|
| WO | WO 93/11747 | 6/1993 |
| WO | WO 93/18746 | 9/1993 |
| WO | WO 94/13262 | 6/1994 |
| WO | WO 94/14490 | 7/1994 |
| WO | WO 94/21228 | 9/1994 |
| WO | WO 94/21229 | 9/1994 |
| WO | WO 95/17195 | 6/1995 |
| WO | WO 96/18384 | 6/1996 |
| WO | WO 96/19198 | 6/1996 |
| WO | 96 19969 | 7/1996 |
| WO | WO 96/19968 | 7/1996 |
| WO | WO 96/32099 | 10/1996 |
| WO | WO 96/32150 | 10/1996 |
| WO | WO 96/32151 | 10/1996 |
| WO | WO 96/32345 | 10/1996 |
| WO | WO 97/47286 | 12/1997 |
| WO | WO 98/01147 | 1/1998 |
| WO | WO 98/03533 | 1/1998 |
| WO | WO 98/05302 | 2/1998 |
| WO | WO 98/13031 | 4/1998 |
| WO | WO 98/24420 | 6/1998 |
| WO | WO 98/34595 | 8/1998 |
| WO | WO 98/34596 | 8/1998 |
| WO | WO 98/56349 | 12/1998 |
| WO | WO 99/12596 | 3/1999 |
| WO | WO 99/64014 | 12/1999 |
| WO | WO 99/65460 | 12/1999 |
| WO | WO 99/65464 | 12/1999 |
| WO | WO 00/06121 | 2/2000 |
| WO | WO 00/07567 | 2/2000 |
| WO | WO 00/23065 | 4/2000 |
| WO | WO 00/30608 | 6/2000 |
| WO | WO 00/35458 | 6/2000 |
| WO | WO 00/53157 | 9/2000 |
| WO | WO 00/78286 | 12/2000 |
| WO | WO 01/47493 | 7/2001 |

OTHER PUBLICATIONS

R.O. Williams III et al, "A study of an epoxy aerosol can lining exposed to hydrofluoroalkane propellants", *European Journal of Pharmaceutics and Biopharmaceutics*, vol. 44, pp. 195-203, (1997).

ABPI Compendium of Data Sheets and Summaries of Product Characteristics, Datapharm Publications Limited, London, pp. 81-82, (1996-97).

Paul A. Sanders, Ph.D., "Homogeneous Systems and Their Properties", *Handbook of Aerosol Technology*, Second Edition, Van Nostrand Reinhold Company, NY, p. 30, 1979.

G. Brambilla et al, "Modulation of Aerosol Clouds Produced by HFA Solution Inhalers", *Portable Inhalers*, pp. 155-159, (Nov. 26 & 27, 1998).

B. Meakin, "Fine Particle Dose Control of Solution Based pMDIs", *Drug Delivery to the Lungs IX*, The Aerosol Society, pp. 1-20, (Dec. 14 & 15, 1998).

Chet Leach, "Enhanced Drug Delivery Through Reformulating MDIs with HFA Propellants-Drug Deposition and Its Effect on Preclinical and Clinical Programs", *Respiratory Drug Delivery V*, 1996, pp. 133-144.

L. Harrison et al, "Twenty-eight-day Double-blind Safety Study of an HFA-134a Inhalation Aerosol System in Healthy Subjects", *J. Pharm. Pharmacol.*, 1996, vol. 48, pp. 596-600.

P. Hoet et al, "Epidemic of liver disease caused by hydrochlorofluorocarbons used as ozone-sparing substitutes of chlorofluorocarbons", *The Lancet*, 1997, vol. 350, pp. 556-559.

J. Daly, Jr., "Properties and toxicology of CFC alternatives", *Aerosol Age*, Feb. 1990, pp. 26-27, 40, 56 and 57.

D. Strobach, "Alternatives to CFCs" Part II, *Aerosol Age*, Jul. 1988, pp. 32-33, 42 and 43.

Tsi-Zong Tzou et al, "Drug Form Selection in Albuterol-Containing Metered-Dose Inhaler Formulations and Its Impact on Chemical and Physical Stability", *Journal of Pharmaceutical Sciences*, 1997, vol. 86, No. 12, pp. 1352-1357.

M.J. Kontny et al, "Issues Surrounding MDI Formulation Development with Non-CFC Propellants", *Journal of Aerosol Medicine*, 1991, vol. 4, No. 3, pp. 181-187.

I. P. Tansey, "Changing to CFC-Free Inhalers: The Technical and Clinical Challenges", *The Pharmaceutical Journal*, 1997, vol. 259, pp. 896-898.

D. Tiwari et al, Compatibility Evaluation of Metered-Dose Inhaler Valve Elastomers with Tetrafluoroethane (P134a), a Non-CFC Propellant, *Drug Development and Industrial Pharmacy*, 1998, vol. 24, No. 4, pp. 345-352.

Handbook of Pharmaceutical Excipients, 3rd Ed., Kibbe Editor, pp. 7-9, 220-222, 234-235 and 560-561.

L. I. Harrison et al, "Pharmacokinetics and Dose Proportionality of Beclomethasone From Three Strengths of A CFC-Free Beclomethasone Dipropionate Metered-Dose Inhaler", *Biopharmaceutics & Drug Disposition*, 1997, vol. 18, No. 7, pp. 635-643.

* cited by examiner

FORMULATIONS OF STEROID SOLUTIONS FOR INHALATORY ADMINISTRATION

The present invention relates to optimized formulations for nebulisation administration containing antiinflammatory glucocorticoids in hydroalcoholic solution and a process for the preparation thereof.

More particularly, the invention relates to formulations for monodose or multidose vials in the form of preservative-free stable solutions, well-tolerated by the patients, of reduced osmolarity and that can effectively be nebulised with the nebulisers currently available on the market.

PRIOR ART

The administration of drugs through nebulisation has been used for many years and is the mainstay of treatment of diseases which hamper breathing, such as asthma and chronic bronchitis.

One of the advantages of the inhalatory route over the systemic one is the possibility of delivering the drug directly at site of action, avoiding any systemic side-effects, thus resulting in a more rapid clinical response and a higher therapeutic index.

Among the various drugs active on the respiratory system, corticosteroids such as beclomethasone dipropionate, fluticasone propionate, flunisolide and budesonide are of great importance. Said drugs may be administered in the form of pressurized aerosols or by using ultrasonic or jet nebulisers.

As far as the administration by jet nebulisers is concerned, usually the steroid is either suspended in micronised form in saline or dissolved in water-alcoholic mixtures in the presence of excipients such as buffering agents, stabilizing agents and preservatives.

In particular, budesonide, one of the steroids most applied by means of this administration route by virtue of its better topical/systemic activity ratio, is commercially available only as an aqueous suspension (Pulmicort®), further containing citric acid, sodium citrate, polysorbate 80 and sodium edetate.

In general, suspensions are intrinsically less homogeneous than solutions; furthermore, problems of physical stability can arise during storage, due to the formation of agglomerates or cakes which are difficult to be redispersed.

Said drawback can in turn give rise to problems of repartition and so of dosage uniformity during the filling of the containers; beside that, the lack of homogeneity could also compromise the correct posology of the drug or at least cause a therapeutically less effective administration, since the transfer of the dose from the container to the nebuliser reservoir by the patient could be incomplete.

Furthermore, the effectiveness of the administration form depends on the deposition of an adequate amount of particles at the site of action. One of the most critical parameters determining the proportion of inhalable drug which will reach the lower respiratory tract of a patient is the size of the particles emerging from the device. In order to ensure an effective penetration into the bronchioli and alveoli and hence ensure a high respirable fraction, the mean aerodynamic diameter (MAD) of the particles should be lower than 6 microns ($\mu$m).

Particles with higher MAD are in fact deposited in the higher respiratory tract, i.e. the oropharynx and may give rise to topical side effects; otherwise they may be absorbed thus giving rise to systemic side effects.

In this respect, it is difficult for aqueous suspensions to maintain a constant particle size distribution during their shelf life; in the prior art (Davis S et al Int J Pharm 1, 303–314, 1978; Tiano S et al Pharm Dev Tech 1, 261–268, 1996; Taylor K et al Int J Pharm 153, 93–104, 1997) it is indeed reported that as environmental humidity conditions change, the suspended particles can grow in size following partial or complete recrystallization of the even small amount of solute dissolved, therefore increasing in MAD; said increase may, in turn, impair both the nebulisation efficiency, which is inversely proportional to the MAD of the particles, and the therapeutical efficacy, as particles with MAD greater than 6 $\mu$m cannot be delivered to the preferential site of action.

Steroids such as beclomethasone or fluticasone can only be acceptably formulated as a suspension.

Other glucocorticosteroids such as budesonide or flunisolide can be also prepared as a solution, but, due to their high lipophilicity, it is not possible to prepare simple solutions having the desired concentration of active ingredient without using a suitable co-solvent such as propylene glycol, glycerol or polyethylene glycol. Said co-solvents are however less volatile than water; consequently, by increasing the osmolarity they decrease the surface tension of the whole solution so slowing down the evaporation rate of the droplets produced by nebulisation. This gives rise to a high percentage of particles of size greater than 6 $\mu$m.

In the solution formulations currently available on the market such as those containing flunisolide, the carrier is usually a mixture of physiological solution (0.9% saline in water) and propylene glycol. The presence of sodium chloride contributes to significantly increase the osmolarity and the ionic strength of the solution which may result in an even higher percentage of non respirable particles, being the formulations not effectively aerosolized by the common nebulizers. An excessive hypertonicity can also induce tolerability problems in the patient, which are paradoxically manifested by cough and bronchospasm (O'Callaghan C et al Lancet, ii, 1424–1425, 1986).

Inhalatory formulations should meet a further important requirement, which is a pharmaceutically acceptable shelf-life. In order to maintain potency, minimize the formation of degradation products and prevent any microbiological contaminations, preservatives and stabilizing agents such as antioxidants and metal chelating agents are frequently used. The prior art reports that some substances commonly used for this purpose can either induce allergic reactions or give rise to irritation of the respiratory mucosas (Menendez R et al J Allergy Clin Immunol 84, 272–274, 1989; Afferty P et al Thorax 43, 446–450, 1988).

Moreover, they further increase the osmolarity.

In view of the potential problems and disadvantages connected with the formulations containing anti-inflammatory glucocorticoids currently available on the market, it would be highly advantageous to provide formulations in solution, containing no stabilizing agents and/or preservatives, provided of adequate shelf life, whose osmolarity permits generation of an effective aerosol well tolerated by patients.

DISCLOSURE OF THE INVENTION

The main object of the present invention is to provide solution formulations containing therapeutically effective concentrations of antiinflammatory glucocorticoids, provided of adequate shelf life, without stabilizing agents and preservatives, well tolerated by patients, which can be effectively aerosolized with the common nebulizers and able to ensure a high respirable fraction by producing active ingredient particles with MAD predominantly ranging from 1 to 6 μm.

More specifically, the present invention aims to provide optimized solutions of budesonide, to be administered through nebulisation, without using preservatives and/or stabilizing agents.

Said aim has been attained by preparing a pharmaceutical formulation, suitable for inhalation through nebulisation, which consists of a solution of a steroid in that:

a) the steroid concentration ranges from 0.01% to 0.1%;

b) the carrier is a mixture of water and propylene glycol in a ratio ranging from 60:40 to 30:70 v/v;

c) pH ranges from 3.5 to 5.0 and has been adjusted by using a concentrated strong acid;

wherein the osmolarity is not more than 7500 mOsm/l, preferably not more than 7000, even more preferably not more than 6800 and the percentage of nebulised active ingredient particles with MAD below 6 μm is higher than 70% and the nebulisation efficiency after 5 minutes is higher than 20%.

In a particular embodiment of the invention, the formulations are prepared by using a carrier consisting of a water: propylene glycol 50:50 v/v mixture, correcting pH with concentrated strong acids such as hydrochloric acid to values preferably ranging from 4 to 5. It has, in fact, been surprisingly found that if pH, instead of being just corrected, is adjusted by addition of the usual saline buffers such as dibasic sodium phosphate/citric acid couple, the solutions do not remain stable for a pharmaceutically acceptable time. After addition of said buffers, under accelerated stability conditions (40° C., 75% relative humidity [R.H.]), a 10% or higher loss of the assay is in fact observed already after three months. Conversely, the assay of the active ingredient in the solutions whose pH has been simply corrected to 4.0 or 4.5 with HCl remains substantially unchanged after 18 months under long term conditions (25° C., 60% R.H.) and only a slight decrease in the assay is observed after 6 months under accelerated conditions. The solutions of the invention require no addition of stabilizing agents such as metal chelating agents or other antioxidants.

Although it is known from the prior art that the stability of steroids bearing a dihydroxyacetone side chain, such as budesonide and flunisolide, depends on pH and that said steroids are more stable within a pH range of 3–5 (Das Gupta V, J Pharm Sci 12, 1453, 1983; Timmins P et al. J Pharm Pharmacol 35, 175, 1983), stable budesonide in solution in a simple water-alcoholic mixture consisting of water and propylene glycol has never been reported; moreover it has never been disclosed that stability depends so dramatically on the way of adjusting the pH.

Analogously it has never been reported that said solutions can be efficaciously delivered by means of a nebulizer to the lower respiratory tract.

The pH of the formulation also affects the tolerability of the nebulised solution. Aerosol formulations with pH ranging from 4 to 5 are recognizedly well tolerated by the patient (Morén F et al, Aerosol in Medicine, Elsevier, Amsterdam, 1993, page 342). Furthermore, the simple correction of pH with strong acids causes a decrease in the buffering properties of the solution thereby allowing the pH of the droplets to readily change and attain more physiologically acceptable values once the pulmonary area has been reached. On the other hand, the correction of the natural pH of the water to lower values is extremely advantageous when the solution is stored in glass ampoules as the pH inside such containers tends to increase during storage thus adversely affecting the stability of the active ingredient.

The only known solution formulation of budesonide commercially available is a lotion for topical use containing almost 80% w/w of alcohols.

This kind of formulation, due to the so high content of alcohols, is clearly not suitable for inhalatory purposes.

EP 794767 (Falk) discloses budesonide solutions at pH below 6 to be used in the preparation of enemas and rectal foams. The formulations are claimed as stable, but actually if we look at the examples only water-alcoholic formulations involving the use of antioxidants such as sodium edetate or complexing agents such as cyclodextrins are stable for a pharmaceutically acceptable time (at least 6 months).

When such preservatives are not present, the assay of the active ingredient decreases by more than 30% already after 4 weeks at 40° C. The minimum stability requirements prescribed by the Guidelines for medicinal products for human use—Quality and biotechnology, Vol 3A, 1998 Edition, pages 127–134, envision a loss of assay of the active ingredient lower than 5% after storage under accelerated conditions (40° C., 75% R.H.) for six months. In EP 794767, simple 0.0033% solutions in water at different pH values, have been tested only after 14 day of storage. Solutions in propylene glycol alone, which is anyway a carrier unsuitable for the administration via nebulisation, are found to be sufficiently stable only at pH 2.8. Therefore EP 794767 does not teach to prepare pharmaceutically acceptable hydro-alcoholic budesonide solution formulation stable without the aid of stabilizing agents which may be efficiently nebulized.

DE 19625027 claims solutions of drugs such as flunisolide and budesonide, stable by addition of an organic or inorganic acid, for the preparation of pressurized aerosols, using as a propellant a carrier containing at least 70% of ethanol. Said solutions, due to the high percentage of ethanol, which is recognisedly irritant, are not suitable for nebulisation and always contain EDTA.

In the solutions of the invention, consisting of a physiologically acceptable selected range of propylene glycol in a ratio to water ranging from 60:40 to 30:70 v/v it is also possible to avoid the use of preservatives, as it is proved by the bioburden which remains within the limits provided for by the European Pharmacopoeia during the whole stability time of the product.

Since the solutions of the invention are stable without the use of stabilizing agents and preservatives, it is possible to keep their osmolarity to a lower value with respect to known solution formulations, in such a way as to give rise to either an improved efficiency of nebulization and an increased fraction of respirable droplets.

It has in fact been found, and this is a further object of the invention, that the formulations consisting of simple water: propylene glycol solutions are more efficiently nebulised than the corresponding solutions containing sodium chloride and/or salts acting as buffering or stabilizing agents. Furthermore, the formulations of the invention can deliver a higher amount of active ingredient with MAD ranging from 1 to 6 μm therefore providing a larger respirable fraction.

Davis S in Int. J. Pharm. 1, 71–83, 1978 reports that when a water propylene glycol mixture is used for nebulising 0.1% of flunisolide, the optimal percentage of glycol to attain efficient nebulisation is around 50–60% v/v, but no teachings as regards the preparation of stable solutions in said carrier without further addition of stabilizing agents or buffering salt is reported. Furthermore, in Int. J. Pharm. 1, 85–83, 1978, in a study aimed at evaluating as a carrier the water-propylene glycol-ethanol system, Davis suggests that the presence of alcohol would increase the total output from the nebuliser. As it can be appreciated from Table 2 of the same paper, the nebulisation efficiency of the solution with no alcohol is indeed rather low (1 ml in 21 min).

Derbacher J (Atemwegs-Lungenkrank 20, 381–82, 1994), in a study which emphasizes the importance of pH and osmolarity of solutions for the inhalatory route, reports, inter alia, a budesonide isotonic solution (282 mosm/l) with pH 4, but no information are given concerning the composition of the carrier. Moreover it is not reported whether either the concentration or stability of the active ingredient are suitable for a pharmaceutical use. It is in any case unlikely that budesonide dissolves in an aqueous medium at a therapeutic concentration, due to its high lipophilicity.

With respect to the prior art, the compositions of the invention are therefore characterized by the following features:
- a steroid, preferably consisting of budesonide in solution at concentrations ranging from 0.001% to 0.1%, preferably from 0.025% to 0.05%;
- a carrier consisting of a water propylene glycol mixture in ratios ranging from 60:40 v/v to 30:70 v/v, preferably 50:50 v/v;
- a pH ranging from 3.5 to 5.0, preferably from 4.0 to 4.5, characterized by a shelf life of at least two years and a reduced osmolarity in such a way as to improve the efficiency of nebulization and the fraction of respirable droplets.

Advantageously the osmolarity is not more than 7500 mOsm/l, preferably not more than 7000, even more preferably not more than 6800, based on the calculation of the depression of the freezing point.

Similar compositions can be prepared with acetonide glucocorticoids and in particular with flunisolide.

Preferred carriers for the formulations of the invention are those consisting of a water: propylene glycol mixture in ratios ranging from 60:40 to 30:70 v/V, preferably in a 50:50 v/v ratio, the concentration of the active ingredient in the solution ranging from 0.001 to 0.1% by weight.

The pH can be corrected by using any concentrated strong acid such as HCl and should range from 3.5 to 5.0, preferably from 4.0 to 4.5. Preferred active ingredients are steroids usually administered in the inhalatory treatment of respiratory diseases. Particularly preferred are acetonide derivatives such as flunisolide. Even more preferred are acetal derivatives such as budesonide or the epimers thereof.

The obtained solutions can be distributed in suitable containers such as multidose vials for nebulisation or preferably in monodose vials, preformed or produced with a technology capable of guaranteeing filling the vials under inert atmosphere. The solution formulations can be advantageously sterilized by filtration.

The formulations of the invention are illustrated in detail by the following examples.

EXAMPLE 1

Preparation of 0.05% Budesonide Solution at pH 4.0 and Stability Studies 5 liters of propylene glycol was poured into a mixer and heated up to a temperature of 40–50° C. 5 g (0.05%) of budesonide was added, mixing for about 30 min. After cooling to room temperature, an equal volume of depurated water was added, stirring for a further 15 minutes. pH of the solution was corrected to 4.0 with 0.1 N HCl. The solution was filtered through a 0.65 mm membrane. The solution was distributed in 2 ml polypropylene monodose vials.

| | Ingredients | |
|---|---|---|
| | Amounts | |
| Components | Total preparation amount | Amount per pharmaceutical unit |
| Budesonide | 5 g | 1 mg |
| Propylene glycol | 5 l | 1 ml |
| Depurated water q.s. to | 10 l | 2 ml |
| 0.1N HCl q.s. to | about pH 4.0 | |

The stability of the vials was evaluated both under long-term (25° C., 60% R.H.) and accelerated conditions (40° C., 75% R.H.) [R.H.=relative humidity]. Results are reported in Tables 1 and 2, respectively. Assays of budesonide and of its main related substances (degradation products) were determined by HPLC.

Microbiological controls were carried out according to Eur. Ph. III Ed.

The formulation of the invention turns out to be stable for at least 18 months of storage and no increase in the bioburden is observed. The assay is higher than 97% under long-term conditions, whereas is higher than 95% under accelerated conditions. pH remains substantially unchanged under both conditions. None of the other technological parameters undergoes alterations.

TABLE 1

Solution of example 1 - Stability under long-term conditions (25° C., 60% R.H.)

| | TECHNOLOGICAL CONTROLS | | CHEMICAL CONTROLS | | Impurities | |
|---|---|---|---|---|---|---|
| Analysis | solution appearance | packaging appearance | Budesonide (g/100 ml) | Assay (%) | and degraded (% area) | pH |
| Confidence limits | Clear colourless solution | Colourless monodose | 0.0450–0.0525 | 95–105 | — | — |
| t = 0 | Clear colourless solution | Colourless monodose | 0.0513 | 100 | 0.83 | 3.92 |
| t = 1 month | Clear colourless solution | Colourless monodose | 0.0507 | 98.8 | 0.60 | 3.89 |

TABLE 1-continued

Solution of example 1 - Stability under long-term conditions (25° C., 60% R.H.)

| Analysis | TECHNOLOGICAL CONTROLS | | CHEMICAL CONTROLS | | | |
| --- | --- | --- | --- | --- | --- | --- |
| | solution appearance | packaging appearance | Budesonide (g/100 ml) | Assay (%) | Impurities and degraded (% area) | pH |
| t = 3 months | Clear colourless solution | Monodose colourless | 0.0514 | 100.2 | 0.82 | 4.00 |
| t = 6 months | Clear colourless solution | Colourless monodose | 0.0507 | 98.8 | 1.58 | 3.91 |
| t = 12 months | Clear colourless solution | Colourless monodose | 0.0510 | 99.4 | 2.17 | 3.85 |
| t = 18 months | Clear colourless solution | Colourless monodose | 0.0500 | 97.5 | 2.47 | 3.92 |

TABLE 2

Solution of example 1 - Stability under accelerated conditions (40° C., 75% R.H.)

| Analysis | TECHNOLOGICAL CONTROLS | | CHEMICAL CONTROLS | | | |
| --- | --- | --- | --- | --- | --- | --- |
| | Solution appearance | Packaging appearance | Budesonide (g/100 ml) | Assay (%) | Impurities and degraded (% area) | pH |
| Confidence limits | Clear colourless solution | Colourless monodose | 0.0450–0.0525 | 95–105 | — | — |
| t = 0 | Clear colourless solution | Monodose colourless | 0.0513 | 100 | 0.83 | 3.92 |
| t = 1 month | Clear colourless solution | Monodose colourless | 0.0504 | 98.2 | 0.84 | 3.88 |
| t = 2 months | Clear colourless solution | Monodose colourless | 0.0506 | 98.6 | 1.55 | 4.01 |
| t = 3 months | Clear colourless solution | Monodose colourless | 0.0501 | 97.7 | 2.00 | 3.97 |
| t = 6 months | Clear colourless solution | Monodose colourless | 0.0491 | 95.7 | 4.07 | 3.89 |

EXAMPLE 2

Preparation of 0.05% Budesonide Solution at pH 4.5 and Stability Tests

According to the process reported in example 1, a solution having the following formula was prepared:

| Components | Total amount of the preparation | Amount per pharmaceutical unit |
| --- | --- | --- |
| Budesonide | 5 g | 1 mg |
| Propylene glycol | 5 l | 1 ml |
| Depurated water q.s. to | 10 l | 2 ml |
| 0.1N HCl q.s. to | about pH 4.5 | — |

The stability of the monodose vials was evaluated both under long-term (25° C., 60% R.H.) and accelerated conditions (40° C., 75% R.H.).

The results are reported in Tables 3 and 4, respectively.

The determination of the parameters was carried out as reported in example 1.

The formulation of the invention turns out to be stable for at least 18 months of storage and no increase in the bioburden is observed. Under long-term conditions the assay is higher than 97%, whereas under accelerated conditions was higher than 96%. pH remains substantially unchanged under both conditions. None of the other technological parameters undergoes alterations.

TABLE 3

Solution of example 2 - Stability under long-term (25° C., 60% R.H.)

| Analysis | TECHNOLOGICAL CONTROLS | | CHEMICAL CONTROLS | | | |
|---|---|---|---|---|---|---|
| | Solution appearance | packaging appearance | Budesonide (g/100 ml) | Assay (%) | Impurities and degraded (% area) | pH |
| Confidence limits | Clear colourless solution | Colourless monodose | 0.0450–0.0525 | 95–105 | — | — |
| t = 0 | Clear colourless solution | Colourless monodose | 0.0508 | 100 | 0.88 | 4.55 |
| t = 1 month | Clear colourless solution | Colourless monodose | 0.0505 | 99.4 | 0.47 | 4.44 |
| t = 3 months | Clear colourless solution | Colourless monodose | 0.0500 | 98.4 | 0.76 | 4.49 |
| t = 6 months | Clear colourless solution | Colourless monodose | 0.0496 | 97.6 | 1.22 | 4.47 |
| t = 12 months | Clear colourless solution | Colourless monodose | 0.0500 | 98.4 | 1.93 | 4.32 |
| t = 18 months | Clear colourless solution | Colourless monodose | 0.0510 | 100.4 | 2.46 | 4.34 |

TABLE 4

Solution of example 2 - Stability under accelerated conditions (40° C., 75% R.H.)

| Analysis | TECHNOLOGICAL CONTROLS | | CHEMICAL CONTROLS | | | |
|---|---|---|---|---|---|---|
| | Solution appearance | Packaging appearance | Budesonide (g/100 ml) | Assay (%) | Impurities and degraded (% area) | pH |
| Confidence limits | Clear colourless solution | Colourless monodose | 0.0450–0.0525 | 95–105 | — | — |
| t = 0 | Clear colourless solution | Colourless monodose | 0.0508 | 100 | 0.88 | 4.55 |
| t = 1 month | Clear colourless solution | Colourless monodose | 0.0502 | 98.8 | 0.79 | 4.42 |
| t = 2 months | Clear colourless solution | Colourless monodose | 0.0511 | 100.6 | 1.62 | 4.75 |
| t = 3 months | Clear colourless solution | Colourless monodose | 0.0496 | 97.6 | 1.95 | 4.48 |
| t = 6 months | Clear colourless solution | Colourless monodose | 0.0497 | 97.8 | 3.8 | 4.44 |

EXAMPLE 3

Stability Comparisons

With a process similar to that described in examples 1 and 2, 0.05% Budesonide reference solutions were prepared whose pH was adjusted by using buffers consisting of different relative percentages of the dibasic sodium phosphate/citric acid couple. Each solution was distributed in 2 ml polypropylene monodose vials (reference solutions 5 to 8). Furthermore, a 0.05% Budesonide solution in saline:propylene glycol 50:50 v/v was prepared whose natural pH was not corrected.

Part of said solution was placed in 2 ml monodose vials (reference solution 4), whereas the remainder was poured into an amber glass ampoule and tightly sealed (reference solution 3).

The vials containing the various solutions and the glass ampoule were stored at 40° C. for 6 months. The Budesonide assay and the pH of said samples were evaluated. Results are reported in Table 5.

From the results obtained with the solutions buffered to different pH values a rather high loss of assay can be appreciated already after three months; said solutions are therefore less stable than those described in examples 1 and 2.

Also the solution at natural pH after 6 month storage in monodose vials was less stable than the solutions described in examples 1 and 2 (see Tables 2 and 4); as far as the same solution is concerned, but stored in an amber glass ampoule, the assay dramatically decreased with an about 20% loss of potency. In this case pH tends to increase during storage to about 6. The loss in the assay is most likely related with the increase of pH.

Therefore the right starting pH value is demonstrated to be of paramount importance for the stability of these formulations. As far as budesonide solutions are concerned, the starting pH needs to be set at a value between 4.0 and 4.5.

It is accordingly possible to determine both the nebulisation efficiency (percentage amount of nebulised active ingredient) and the parameters useful to define the respirable fraction, namely the fine particle fraction (amount and relative % of particles of active ingredient of size below 6.8 mm) and extra fine particle fraction (amount and relative % of particles of active ingredient of size below 3 $\mu$m).

Monodose vials of the formulation currently available on the market as an aqueous suspension (Pulmicort®) and monodose vials containing the solution 4 of example 3 (saline: propylene glycol 50:50 v/v) were nebulised for comparison. Results are reported in Table 6 as a mean of three determinations.

TABLE 6

| | Amount of nebulised | Fine particle fraction | | Extrafine particle fraction | | Efficiency |
|---|---|---|---|---|---|---|
| | a.i., $\mu$g | $\mu$g | (%) | $\mu$g | (%) | (%) |
| Solution of ex. 1 | 366 | 317 | (86.7) | 172 | (47.2) | 31.7 |
| Solution 4 of ex. 3 | 259 | 224 | (86.5) | 127 | (49.0) | 27.2 |
| Pulmicort ® | 103 | 85 | (82.5) | 47 | (45.6) | 14.3 | a.i. = active ingredient

The results show a significant improvement in terms of nebulisation efficiency and fine and extrafine fractions delivered for the solution of the invention compared with respect to the commercial formulation. An appreciable improvement of said parameters is also observed with respect to the solution in saline: propylene glycol 50:50 v/v (solution 4 of ex. 3).

TABLE 5

Comparison solutions of Example 3

| Solution | Time 0 | | 1 month | | 2 months | | 3 months | | 6 months | |
|---|---|---|---|---|---|---|---|---|---|---|
| | (%) | pH | (%) | pH | (%) | pH | (%) | pH | (%) | pH |
| Sol. 3 - pH 5.7 (glass)* | 100.0 | 5.7 | 77.4 | 6.4 | — | — | 60.8 | 6.6 | 52.5 | 6.1 |
| Sol. 4 - pH 4.7 (monodose)* | 100.0 | 4.7 | 98.6 | 4.7 | — | — | 96.6 | 4.8 | 93.6 | 4.7 |
| Sol. 5 - pH 5.20 buffer | 100.0 | 5.2 | — | 5.2 | — | | 89.1 | 5.3 | — | |
| Sol. 6 - pH 4.26 buffer | 100.0 | 4.3 | 97.4 | 4.3 | 95.0 | 4.3 | 93.7 | 4.4 | 80.4 | 4.4 |
| Sol. 7 - pH 4.01 buffer | 98.6 | 4.0 | 96.8 | 4.0 | 94.9 | 4.0 | 91.9 | 4.0 | — | — |
| Sol. 8 - pH 3.36 buffer | 99.1 | 3.3 | 96.7 | 3.3 | 94.8 | 3.4 | 90.7 | 3.4 | — | — |

*natural pH (neither corrected nor buffered)

EXAMPLE 4

The nebulisation performances of the solution for inhalation described in example 1 were evaluated by multi-stage liquid impinger (M.S.L.I.) analysis, according to the procedure described in Eur. Ph. III Ed., 1997, using a commercial jet nebuliser (PARI-BOY) for a 5 minute nebulisation time. The M.S.L.I. apparatus consists of a number of glass elements mutually connected to form chambers capable of separating the droplets depending on their aerodynamic size. As follows, particles with different size deposit in the various separation chambers.

EXAMPLE 5

The size profile of the droplets produced by nebulisation of the solutions described in examples 1 and 2 was determined by API Aerosizer analysis, using a commercial jet nebuliser (PARI-BOY).

The particle size distribution profile of solution 4 in saline: propylene glycol 50:50 v/v described in example 3 was determined for comparison.

Results are reported in Table 7 as diameter ($\mu$m) below which respectively 10%, 50% and 90% of the droplets are included.

TABLE 7

|  | Median aerodynamic diameter of the droplets [MAD] (μm) | | |
|---|---|---|---|
|  | 10% | 50% | 90% |
| Solution of ex. 1 | 2.26 | 3.86 | 5.79 |
| Solution of ex. 2 | 2.03 | 3.29 | 4.79 |
| Solution 4 of ex. 3 | 3.31 | 5.21 | 7.48 |

The results show a significant shift towards lower values of the size profile of the droplets produced by nebulisation of the solutions of the invention compared with those of the solution in saline: propylene glycol 50:50 v/v (solution 4 of ex. 3).

What is claimed is:

1. A stable pharmaceutical formulation for inhalation through nebulisation consisting of a solution of a steroid in which:
   a) the steroid concentration ranges from 0.01% to 0.1%;
   b) the liquid component of the solution is a mixture of water and propylene glycol in a ratio ranging from 60:40 to 30:70 v/v; and
   c) the pH ranges from 3.5 to 5.0, the pH of the formulation having been adjusted by the addition of a concentrated strong acid to the solution; wherein the percentage of nebulised active ingredient particles with MAD below 6 μm is higher than 70% and the nebulisation efficiency is higher than 20%.

2. The formulation according to claim 1, wherein the liquid component of the solution consists of water and propylene glycol in a 50:50 v/v ratio.

3. The formulation according to claim 1, wherein the pH of the solution ranges from 4.0 to 4.5 and has been adjusted by the addition of HCl to the solution.

4. The formulation according to claim 1, wherein the steroid is in the form of an acetal or is in the form of an acetonide.

5. The formulation according to claim 4, wherein the steroid in the form of an acetal is budesonide.

6. The formulation according to claim 4, wherein the steroid in the form of an acetonide is flunisolide.

7. The formulation according to claim 5, wherein the concentration of budesonide in the solution ranges from 0.025 to 0.05%.

8. The formulation according to claim 6, wherein the concentration of flunisolide in the solution is 0.1%.

9. The formulation according to claim 1, wherein the osmolarity of the solution is not more than 7500 mOsm/l.

10. The formulation according to claim 9, wherein the osmolarity of the solution is not more than 7000 mOsm/l.

11. A process for the preparation of pharmaceutical formulations according to claim 1, which comprises:
    a) preparing a propylene glycol solution of a steroid at a temperature of 40 to 50° C.;
    b) cooling the solution, and then diluting the solution with water;
    c) adjusting the pH of the solution by the addition of a concentrated, strong acid thereto; and
    d) filtering the solution and distributing the solution to containers for the treatment of individuals by nebulisation.

12. The process according to claim 11, wherein the pH of the solution is adjusted to a range of 3.5 to 5.0.

13. The process according to claim 11, wherein the propylene glycol solution of the steroid is diluted with water to a water and propylene glycol ratio ranging from 60:40 to 30:70 v/v.

14. The process according to claim 11, wherein the strong acid is hydrochloric acid.

* * * * *